(12) United States Patent
Yoon et al.

(10) Patent No.: US 9,169,354 B2
(45) Date of Patent: *Oct. 27, 2015

(54) MULTIFUNCTIONAL FORMS OF POLYOXAZOLINE COPOLYMERS AND DRUG COMPOSITIONS COMPRISING THE SAME

(75) Inventors: Kunsang Yoon, Madison, AL (US); J. Milton Harris, Huntsville, AL (US); Michael David Bentley, Huntsville, AL (US)

(73) Assignee: Serina Therapeutics, Inc., Huntsville, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/367,128

(22) Filed: Feb. 6, 2012

(65) Prior Publication Data

US 2012/0136123 A1 May 31, 2012

Related U.S. Application Data

(62) Division of application No. 12/744,472, filed as application No. PCT/US2009/030762 on Jan. 12, 2009, now Pat. No. 8,110,651.

(60) Provisional application No. 61/020,684, filed on Jan. 11, 2008, provisional application No. 61/029,337, filed on Feb. 16, 2008.

(51) Int. Cl.
*C08G 73/06* (2006.01)
*C08G 73/02* (2006.01)
*C08G 75/02* (2006.01)
*C08G 69/00* (2006.01)

(52) U.S. Cl.
CPC .......... *C08G 73/0233* (2013.01); *C08G 73/028* (2013.01)

(58) Field of Classification Search
CPC .................................................. C08G 73/06
USPC ........................... 528/321, 373, 403; 525/410
See application file for complete search history.

(56) References Cited

U.S. PATENT DOCUMENTS

| | | | |
|---|---|---|---|
| 4,709,039 A | 11/1987 | Chou | |
| 5,130,126 A | 7/1992 | Koyama et al. | |
| 5,416,071 A | 5/1995 | Igari et al. | |
| 5,635,571 A | 6/1997 | Frechet et al. | |
| 5,643,575 A | 7/1997 | Martinez et al. | |
| 5,932,462 A | 8/1999 | Harris et al. | |
| 6,340,742 B1 | 1/2002 | Burg et al. | |
| 6,583,272 B1 | 6/2003 | Balion et al. | |
| 6,608,183 B1 | 8/2003 | Cox et al. | |
| 6,753,165 B1 | 6/2004 | Cox et al. | |
| 6,908,963 B2 | 6/2005 | Roberts et al. | |
| 7,074,755 B2 | 7/2006 | Heavner | |
| 7,077,939 B1 | 7/2006 | Crooks et al. | |
| 7,125,843 B2 | 10/2006 | DeFrees et al. | |
| 7,128,913 B2 | 10/2006 | Burg et al. | |
| 7,148,333 B2 | 12/2006 | Cox et al. | |
| 7,385,028 B2 | 6/2008 | Miao et al. | |
| 7,399,839 B2 | 7/2008 | Cox et al. | |
| 8,101,706 B2 * | 1/2012 | Yoon et al. | 528/321 |
| 8,110,651 B2 * | 2/2012 | Yoon et al. | 528/321 |
| 2002/0075448 A1 | 6/2002 | Kunzler et al. | |
| 2002/0081734 A1 | 6/2002 | Choi et al. | |
| 2002/0115833 A1 | 8/2002 | Burg et al. | |
| 2003/0191291 A1 | 10/2003 | Kochendoerfer et al. | |
| 2004/0082765 A1 | 4/2004 | Nakamura et al. | |
| 2004/0266690 A1 | 12/2004 | Pool | |
| 2006/0051315 A1 | 3/2006 | Scaria et al. | |
| 2006/0276634 A1 | 12/2006 | Nakamura et al. | |
| 2010/0069579 A1 | 3/2010 | Harris et al. | |

FOREIGN PATENT DOCUMENTS

| | | |
|---|---|---|
| WO | WO/90/12874 | 1/1990 |
| WO | WO/01/76639 | 10/2001 |
| WO | WO/03/066069 | 8/2003 |
| WO | WO/2007/010552 | 1/2007 |

OTHER PUBLICATIONS

Hsiue, GH; "Nonviral Gene Carriers Based on Diblock Copolymers of Poly (2-ethyl-2-oxazoline) and Linear Polyethylenimine"; Bioconjung Chem. May-Jun. 2006; 17(3):781-6.
Baharlou, Simin "International Preliminary Report on Patentability"; The International Bureau of WIPO Jul. 13, 2010.
Cesana, Sonia et al. "First Poly (2-oxazoline)s with Pendant Amino Groups", Macromolecular Chemistry and Physics, pp. 183-192, vol. 207, Jan. 2006.
Luxenhofer, R. "Novel Functional Poly (2-oxazoline)s as Potential Carriers for Biomedical Applications", Dissertation, Technical University, Munich, 2007.
Adams, Nico, et al. "Poly (2-oxazolines) in biological and biomedical application contexts", Advanced Drug Delivery Reviews, pp. 1504-1520, vol. 59, Dec. 2007.
Oscar Nuyken, et al. "Amphiphillic Polymers Based on Poly (2-oxazoline)s—From ABC-Triblock Copolymers to Micellar Catalysis", Macromolecular Symposis, pp. 215-230, vol. 215, International Union of Pure and Applied Chemistry, Aug. 1, 2004.
Chujo, et al. "Synthesis of Triethoxysillyl-Terminated Polyoxazolines and their Cohydrolysis Polymerization with Tetraethoxysilane", Macromolecules, pp. 5681-5686, vol. 30, 1993, U.S.

(Continued)

*Primary Examiner* — Duc Truong
(74) *Attorney, Agent, or Firm* — Thomas G. Peterson; Bradley Arant Boult Cummings LLP

(57) ABSTRACT

The present disclosure provides copolymers of 2-substituted-2-oxazolines possessing two or three reactive functional groups which are also chemically orthogonal. The copolymers described may be random copolymers, block copolymers or a mixture of random and block copolymer configurations. Furthermore, the present disclosure provides novel methods for synthesizing the above polymers and for conjugating to molecules such as targeting, diagnostic and therapeutic agents.

10 Claims, No Drawings

(56) References Cited

OTHER PUBLICATIONS

Roberts, et al., "Chemistry for Peptide and Protein PEGylation", Advanced Drug Reviews, pp. 459-476, vol. 54, 2002, U.S.

Tsutsumiuchi, et al., "Synthesis of Polyloxazoline-(Glyco)peptide Block Copolymers by Ring-Opening Polymerization of (Sugar-Substituted) a-Amino Acid N-Carboxyanhydrides with Polyoxazoline Macroinitiators", Macromolecules, pp. 4013-4017, vol. 30, Jun. 1997, U.S.

Velander, et al., "Polyoxazoline-Peptide Adducts that Retain Antibody Avidity", Biotechnology and Bioengineering, pp. 1024-1030, vol. 39, Apr. 1992, U.S.

Waschinski, et al., Poly(oxazoline)s with Telechelic Antimicrobial Functions, Biomacromolecules, pp. 235-243, vol. 6, Nov. 13, 2004.

Hsiue, GH "Nonviral Gene Carriers Based on Diblock Copolymers of Poly (2-ethyl-2-oxazoline) and Linear Polyethylenimine", Biocanjung Chem., pp. 781-786, vol. 17(3), May-Jun. 2006.

West, Nuki "Extended European Search Report"; The European Patent Office Sep. 2, 2011.

Nuki West "European Search Report—European patent application No. 13181892.4" Oct. 4, 2013; pp. 1-6.

Oskar Nuyken, et al. "Amphiphilic Polymers Based on Poly (2-oxazoline)s—From ABC-Triblock Copolymers to Micellar Catalysis" Macromolecular Symposia, vol. 215, No. 1; Aug. 1, 2004, pp. 215-230.

* cited by examiner

MULTIFUNCTIONAL FORMS OF POLYOXAZOLINE COPOLYMERS AND DRUG COMPOSITIONS COMPRISING THE SAME

The present application is a divisional of application Ser. No. 12/744,472 (filed (May 24, 2010), now U.S. Pat. No. 8,110,651 which is the national stage of International Application No. PCT/US2009/030762 (filed Jan. 12, 2009), which claims the benefit of U.S. Provisional Application No. 61/020,684 (filed Jan. 11, 2008) and U.S. Provisional Application No. 61/029,337 (filed Feb. 16, 2008).

FIELD OF THE DISCLOSURE

The present disclosure relates to multifunctional copolymers of polyoxazolines, methods of synthesis and intermediate compounds useful in producing such polyoxazoline derivatives, and conjugates of these polyoxazolines with therapeutic, diagnostic and biological-targeting molecules produced using such polyoxazoline derivatives.

BACKGROUND

Polymer-modified therapeutics have proven to be of great utility in modern pharmaceutical science. Because of the success of polymer-modified therapeutics, it is of interest to expand the range of polymers suitable for such applications, especially to provide polymers having properties not possessed by polymers of the prior art. A need exists for water-soluble, non-toxic polymers which can be used to prepare desired conjugates with target molecules. A need also exists for such polymers with multiple functionalities for use in preparing desired conjugates with multiple molecules (such as, but not limited to, targeting moieties, therapeutic moieties and diagnostic moieties). Using such polymers with multiple functionalities would allow the production of conjugates containing one or more diagnostic and/or therapeutic moiety or conjugates containing a mixture of distinct diagnostic and/or targeting moieties. The present disclosure provides heterofunctional polyoxazoline compounds which provide ready coupling to a range of molecules, such as but not limited to, targeting, therapeutic and/or diagnostic moieties.

DETAILED DESCRIPTION

Definitions

As used herein, the term "POZ" or "POZ polymer" refers to a polymer of 2-substituted-2-oxazoline containing a repeating unit having the structure —[N(COR$_2$)CH$_2$CH$_2$]$_n$— in which R$_2$ is independently selected for each repeating unit from an unsubstituted or substituted alkyl, alkenyl, aralkyl or heterocyclylalkyl group and n is from 3-1000; in one embodiment, the unsubstituted or substituted alkyl, alkenyl, aralkyl or heterocyclylalkyl groups comprise from 1-10 carbon atoms.

As used herein, the term "PMOZ" refers to POZ with the repeating unit having the structure —[N(COCH$_3$)CH$_2$CH$_2$]$_n$—.

As used herein, the term "PEOZ" refers to POZ with the repeating unit having the structure —[N(COCH$_2$CH$_3$)CH$_2$CH$_2$]$_n$—.

As used herein, the term M-POZ, M-PMOZ or M-PEOZ refers to the polymers above in which the nitrogen of the initiating monomer unit is bound to methyl.

As used herein, the term "POZ derivative" or "polyoxazoline derivative" refers to a structure comprising a POZ polymer, the POZ polymer having at least one functional group capable of forming a linkage, directly or indirectly, with a chemical group on a target molecule, a linker or a branching moiety.

As used herein, the term "target molecule" refers to any molecule having therapeutic or diagnostic application or a targeting function, wherein the target molecule is capable of reacting with a functional group on a POZ polymer or a POZ derivative of the present disclosure, including, but not limited to, a drug, a diagnostic agent, a targeting molecule, an organic small molecule, an oligonucleotide, a polypeptide, an antibody or antibody fragment or a protein.

As used herein, the term "target molecule-POZ conjugate" refers to a conjugate of a POZ derivative of the present disclosure and at least one target molecule.

As used herein, the term "hydrolytically stable target molecule-POZ conjugate" refers to a conjugate of a POZ derivative of the present disclosure and at least one target molecule, such that all the chemical linkages in the conjugate are hydrolytically stable.

As used herein, the term "hydrolytically stable" refers to a linkage that is stable in aqueous solutions under physiological conditions; in one embodiment, such linkages are stable for at least 12 hours, 24 hours, 48 hours, 96 hours, 192 hours or greater; in an alternate embodiment such linkages are stable indefinitely.

As used herein, the term "hydrolytically unstable" refers to a linkage that is not stable in aqueous solutions under physiological conditions.

As used herein, the term "physiological conditions" refers to an aqueous solution having a pH from 6-8 and a temperature from 30-42 degrees Celsius.

As used herein, the term "functional group" refers to those groups that will react with a corresponding group, including those groups that will react readily with electrophilic or nucleophilic groups, in contrast to those groups that require strong catalysis or impractical reaction conditions in order to react.

As used herein, the term "link", "linked" "linkage" or "linker" when used with respect to a POZ derivative described herein, or components thereof, refers to groups or bonds that normally are formed as the result of a chemical reaction and typically are covalent linkages.

As used herein, the term "protected" with respect to hydroxyl groups, amine groups, sulfhydryl groups and other reactive groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, various alkyloxycarbonyls, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

As used herein, the team "alkyl", whether used alone or as part of a substituent or linking group, includes straight hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$) (CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH (CH$_2$CH$_3$)$_2$, —CH$_2$C(CH$_3$)$_3$, —CH$_2$C(CH$_2$CH$_3$)$_3$, —CH (CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$) CH$_2$CH(CH$_3$)$_2$, —CH(CH$_3$)CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above.

As used herein, the term "alkylene", whether used alone or as part of a substituent group, includes any group obtained by removing a hydrogen atom from an alkyl group; an alkylene group forms two bonds with other groups.

As used herein, the term "alkenyl", whether used alone or as part of a substituent group, includes an alkyl group having at least one double bond between any two adjacent carbon atoms.

As used herein, the term "alkynyl", whether used alone or as part of a substituent group, includes an alkyl group having at least one triple bond between any two adjacent carbon atoms.

As used herein, the term "unsubstituted alkyl", "unsubstituted alkenyl", and "unsubstituted alkynyl" refers to alkyl, alkenyl and alkynyl groups that do not contain heteroatoms.

The phrase "substituted alkyl", "substituted alkenyl", and "substituted alkynyl" refers to alkyl, alkenyl and alkynyl groups as defined above in which one or more bonds to a carbon(s) or hydrogen(s) are replaced by a bond to non-hydrogen or non-carbon atoms such as, but not limited to, a halogen atom in halides such as F, Cl, Br, and I; and oxygen atom in groups such as carbonyl, carboxyl, hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, enamines imines, oximes, hydrazones, and nitriles; a silicon atom in groups such as in trialkylsilyl groups, dialkylarylsilyl groups, alkyldiarylsilyl groups, and triarylsilyl groups; and other heteroatoms in various other groups. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl) (heterocyclyl)-amine, (aryl)(heterocyclyl)amine, or diheterocyclylamine group.

As used herein, the term "unsubstituted aryl" refers to monocyclic or bicyclic aromatic hydrocarbon groups having 6 to 12 carbon atoms in the ring portion, such as, but not limited to, phenyl, naphthyl, anthracenyl, biphenyl and diphenyl groups, that do not contain heteroatoms. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Unsubstituted aryl groups may be bonded to one or more carbon atom(s), oxygen atom(s), nitrogen atom(s), and/or sulfur atom(s) in the parent compound, however.

As used herein, the term "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms, such as, but not limited to, those atoms described above with respect to a substituted alkyl, and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

As used herein, the term "unsubstituted aralkyl" refers to unsubstituted or substituted alkyl, alkenyl or alkynyl groups as defined above in which a hydrogen or carbon bond of the unsubstituted or substituted alkyl, alkenyl or alkynyl group is replaced with a bond to an aryl group as defined above. For example, methyl (CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group).

As used herein, the term "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members, as compounds such as 2-methylbenzimidazolyl are "substituted heterocyclyl" groups as defined below. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl, tetrazolyl; saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl; saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

As used herein, the term "substituted heterocyclyl" has the same meaning with respect to unsubstituted heterocyclyl groups that substituted alkyl groups had with respect to unsubstituted alkyl groups. However, a substituted heterocyclyl group also includes heterocyclyl groups in which one of the carbons is bonded to one of the non-carbon or non-hydrogen atom, such as, but not limited to, those atoms described above with respect to a substituted alky and substituted aryl groups and also includes heterocyclyl groups in which one or more carbons of the heterocyclyl group is bonded to a substituted and/or unsubstituted alkyl, alkenyl, alkynyl or aryl group as defined herein. This includes bonding arrangements in which two carbon atoms of an heterocyclyl group are bonded to two atoms of an alkyl, alkenyl, or alkynyl group to define a fused ring system. Examples, include, but are not limited to, 2-methylbenzimidazolyl, 5-methylbenzimidazolyl, 5-chlorobenzthiazolyl, 1-methyl piperazinyl, and 2-chloropyridyl among others.

As used herein, the term "unsubstituted heterocyclylalkyl" refers to unsubstituted or substituted alkyl, alkenyl or alkynyl groups as defined above in which a hydrogen or carbon bond of the unsubstituted or substituted alkyl, alkenyl or alkynyl group is replaced with a bond to a heterocyclyl group as defined above. For example, methyl ($CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

As used herein, the term "substituted heterocyclylalkyl" has the same meaning with respect to unsubstituted heterocyclylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

General Description

Polyoxazolines (POZ) are polymers prepared from 2-substituted-2-oxazoline monomers. These polymers are water soluble and have been reported to be nontoxic in mammalian model systems. POZ is generally prepared by reaction of the appropriate stoichiometric amount of 2-alkyl-2-oxazoline with an electrophilic initiator, such as methyl triflate ($CH_3$—$OSO_2$—$CF_3$) or a strong acid such as triflic acid or p-toluenesulfonic acid, followed by termination with a nucleophile such as, but not limited to, hydroxide, a thiol or an amine. The polymer produced is conveniently described in shorthand with the initiating group designated by the leftmost group and the terminating group designated by the rightmost group, with the 2-alkyl-2-oxazoline component in the middle. Therefore, when this shorthand description is used in the current specification, it is intended that the left side of the designation presents the "initiator end" and the right side of the designation presents the "termination end", unless designated otherwise.

For example, when the 2-alkyl-2-oxazoline is 2-methyl-2-oxazoline, methyl triflate is used as the initiator and hydroxide is used as the terminator, the following POZ is produced:

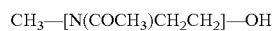

$CH_3$—[N(COCH$_3$)CH$_2$CH$_2$]—OH

The polymer above is conveniently described in shorthand notation as M-PMOZ-OH, in which the methyl initiator is designated by the leftmost M, PMOZ represents polymethyloxazoline with the methyl of the repeating unit designated by the M of PMOZ, and the terminating hydroxyl is designated by the —OH.

Another commonly used monomer is 2-ethyl-2-oxazoline, which with methyl triflate initiation and hydroxide termination would provide the following POZ polymer:

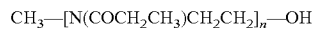

$CH_3$—[N(COCH$_2$CH$_3$)CH$_2$CH$_2$]$_n$—OH

The polymer above is conveniently described in shorthand notation as M-PEOZ-OH, in which the methyl initiator is designated by the leftmost M, PEOZ represents polymethyloxazoline with the ethyl of the repeating unit designated by the E of PEOZ, and the terminating hydroxyl is designated by the —OH.

The degree of polymerization, n, for well characterized polymers can range from approximately 3 to about 1000.

The polymerization process is referred to as a living, cationic polymerization since initiation with an electrophile produces an oxazolinium cation that then reacts in a chain reaction with additional monomer units to produce a growing, "living" cation.

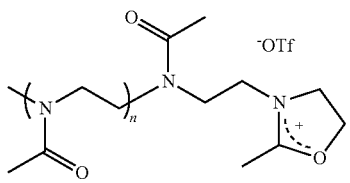

One can predict the products of termination by assuming that the living cation can be represented in the following non-cyclic form (for polymerization of 2-methyl-2-oxazoline initiated with methyl triflate), although in reality the cyclic form is certainly the most important:

In the current discussion we will represent this cation as M-PMOZ$^+$. As noted above, this POZ cation can be "terminated" by reacting with nucleophiles such as hydroxide, thiols or amines.

Oxazoline polymerization can also be initiated with functional electrophiles. For example the electrophilic initiator ethyl 3-bromopropionate has been used to initiate 2-ethyl-2-oxazoline polymerization. Termination with hydroxide gives the following polymer:

Yet another route to preparing polyoxazolines with functional groups is to copolymerize a monomer such as 2-ethyl-2-oxazoline with an oxazoline monomer having a functional group in the 2-position (F. C. Gaertner, R. Luxenhofer, B. Blechert, R. Jordan and M. Essler, J. Controlled Release, 2007, 119, 291-300). For example, Jordan and colleagues have prepared oxazolines with acetylenes and protected aldehydes, carboxylic acids and amines in the 2-position. Copolymerization of these functional monomers with 2-ethyl-2-oxazoline gives random copolymers with multiple pendent or side-chain functional groups. For example, initiation with methyl triflate of polymerization of 2-ethyl-2-oxazoline and 2-pentynyl-2-oxazoline, followed by termination with piperazine (NHC$_4$H$_8$NH) gives the following random copolymer:

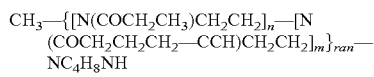

The subscript "ran" indicates that the polymer is a random copolymer. Values of n are typically around 20-30 while m is around 2-5.

These copolymers with pendent functional groups and a terminal functional group are useful in that the pendent and terminal functional groups can be "chemically orthogonal" functional groups. Chemically orthogonal functional groups are those functional groups that will not react with each other but will react selectively with other functional groups. For example, the molecule above has two functional groups, a terminal secondary amine and pendent acetylenes. The acetylene will not react with the amine but will, for example, react with an azide group (—N$_3$). Similarly, the amine will not react with acetylene or azide but will react with, for example, an isothiocyanate group (—NCS). Jordan has used this copolymer to couple an azide-functionalized RGD peptide to the acetylene group, and an isothiocyanate-functionalized metal chelator to the amine. The RGD peptide is known to target tumors, and a diagnostic or therapeutic radionuclide can bind to the chelating group. The final conjugate can be used to image or treat tumors (R. Luxenhofer, M. Lopez-Garcia, A. Frannk, H. Kessler and R. Jordan, Proceedings of the American Chemical Society, PMSE Prepr. 2006, 95, 283-284).

One problem hindering use of the above piperazine- or piperidine-terminated polyoxazolines is that they are difficult to purify. This difficulty arises because contaminating water present during termination leads to nucleophilic attack by water and consequent formation of secondary amine impurity (O. Nuyken, G. Maier, A. Gross, Macromol. Chem. Phys. 197, 83-95, 1996). Since the products from piperazine and piperidine termination always contain a tertiary amine, ion-exchange chromatography cannot be used to remove the contaminating secondary amine.

Still another limitation of the pendent polyoxazolines illustrated above is that these compounds possess a single terminal functional group. Consequently, this structural configuration limits the number of drug or targeting moieties that can be attached to the terminus, whereas effective use of such compounds for therapeutic diagnostic and targeting applications may require multiple loading of these moieties. The polymers of the current disclosure avoid this limitation by providing for multiple copies of each of two chemically reactive and orthogonal functional groups.

Novel Heterofunctional Polyoxazoline Derivatives

The present disclosure avoids the limitations of the prior art by providing heterofunctional polyoxazoline derivatives of two 2-substituted-2-oxazolines comprising at least two functional groups which are chemically reactive and chemically orthogonal to one another. The heterofunctional polyoxazoline derivatives may contain additional functional groups as well. In certain embodiments, all functional groups are chemically orthogonal to one another, while in other embodiments, the additional functional groups may be chemically orthogonal to at least one other functional group present on the heterofunctional polyoxazoline derivative.

Single-Arm Heterofunctional Polyoxazoline Derivatives

In one embodiment, the heterofunctional polyoxazoline derivative is represented by the general structure:

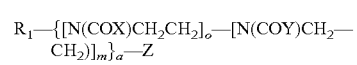

wherein:

R$_1$ is an initiating group;

X is a pendent moiety containing a first functional group;

Y is a pendent moiety containing a second functional group;

Z is a terminating nucleophile; in certain embodiments Z is inert (i.e., does not contain a functional group); in other embodiments, Z contains a third functional group;

a is ran which indicates a random copolymer or block which indicates a block copolymer; and o and m are each an integer independently selected from 1-50.

Exemplary initiating groups include, but are not limited to, hydrogen, alkyl, substituted alkyl, aralkyl, or substituted aralkyl groups. In a particular embodiment, the initiating group is a methyl group. The $R_1$ group is selected to lack a functional group. Additional exemplary initiating groups are disclosed in PCT Application No. PCT/US2008/078159, which is hereby incorporated by reference for such teaching.

As shown by the general structure above, the heterofunctional polyoxazoline derivative comprises at least two functional groups. The first and second functional groups are present on the pendent moieties X and Y, respectively. In certain embodiment, a third functional group is present on the Z group; however, the presence of the third functional group is optional and in some embodiments Z may be inert (i.e., lacking the third functional group).

X and Y are pendent moieties bearing first and second functional groups, respectively. In certain embodiments, X and Y may contain a linking portion that links the first and second functional groups to the polyoxazoline derivative. Exemplary linking portions include alkylene groups. In certain cases, the alkylene group is a $C_1$-$C_{15}$ alkylene group. The linking portions of X and Y may be the same or may be different. For example, both X and Y may contain a $C_5$ alkylene group as the linking portion or X may contain a $C_5$ alkylene group as the linking portion and Y may contain a $C_8$ alkylene group as the linking portion.

The first and second functional groups are chemically orthogonal to one another. The first and second functional groups include, but are not limited to, alkyne, amine, oxyamine, aldehyde, ketone, acetal, ketal, maleimide, ester, carboxylic acid, activated carboxylic acid (such as, but not limited to, N-hydroxysuccinimidyl (NHS) and 1-benzotriazineyl active ester), an active carbonate, a chloroformate, alcohol, azide, vinyl sulfone, or orthopyridyl disulfide (OPSS), provided that the selection is made for X and Y so that the first and second functional groups are chemically orthogonal to one another.

As discussed above, Z may contain a third functional group or be inert. In those embodiments where Z contains a third functional group, the third functional group may be chemically orthogonal to one or both of the first and second functional groups. Exemplary third functional groups include, but are not limited to, alkyne, amine, oxyamine, aldehyde, ketone, acetal, ketal, maleimide, ester, carboxylic acid, activated carboxylic acid (such as, but not limited to, N-hydroxysuccinimidyl (NHS) and 1-benzotriazineyl active ester), an active carbonate, a chloroformate, alcohol, azide, vinyl sulfone, or orthopyridyl disulfide (OPSS).

In a particular embodiment, Z contains the third functional group and is represented by the structure —S—U—W, wherein S is a sulphur atom, U is a linking group and W is the third functional group. In this embodiment, representative U groups include alkylene groups. In a particular embodiment, U is —$(CH_2)_p$— where p is an integer selected from 1 to 10. In a particular embodiment, W may be a carboxylic acid, a protected carboxylic acid, an active ester, an amine or a protected amine. Furthermore, W may be selected from the groups described above for Z. As discussed herein, the third functional group may be chemically orthogonal to one or both of the first functional groups.

Embodiments of the foregoing include but are not limited to:

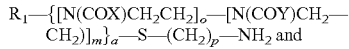

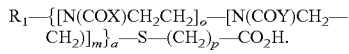

In an alternate embodiment, Z lacks the third functional group and is represented by the structure —S-T-V, wherein S is a sulphur atom, T is a linking group and V is an inert group. In this embodiment, representative T groups include alkylene groups. In a particular embodiment, T is —$(CH_2)_p$— where p is an integer selected from 1 to 10. V may be any inert group. In a particular embodiment, V is —$CO_2CH_3$ or —$C_6H_5$.

Embodiments of the foregoing include but are not limited to:

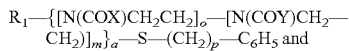

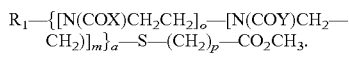

In an alternate embodiment, the heterofunctional polyoxazoline derivative is represented by the general structure below.

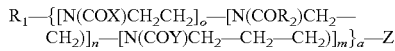

wherein:

$R_1$, X, Y, Z, o, m and a are as defined above;

$R_2$ lacks a functional group and is independently selected for each repeating unit from an unsubstituted or substituted alkyl, an unsubstituted or substituted alkenyl, an unsubstituted or substituted aralkyl or an unsubstituted or substituted heterocyclylalkyl group.

In this embodiment, an additional 2-alkyl-2-oxaxoline is introduced as a third co-monomer. This third 2-alkyl-2-oxaxoline co-monomer lacks a functional group and provides a chemically unreactive spacer between the first and second functional groups present on X and Y, respectively. Such a configuration prevents the first and second functional groups from being sterically hindered.

In certain embodiment, o and m are not zero and the heterofunctional polyoxazoline derivative contains first and second functional groups on X and Y respectively. The first and second functional groups may be selected from the groups described above. As above, the first and second functional groups are chemically orthogonal to one another.

The Z group, as discussed above may contain a third functional group or be inert. In those embodiments where Z contains a third functional group, the third functional group may be chemically orthogonal to one or both of the first and second functional groups. When Z contains the third functional group, the third functional group may be selected from the groups described above.

In a particular embodiment, Z contains the third functional group and is represented by the structure —S—U—W, wherein S is a sulphur atom, U is a linking group and W is the third functional group. In this embodiment, representative U groups include alkylene groups. In a particular embodiment, U is —$(CH_2)_p$— where p is an integer selected from 1 to 10. In a particular embodiment, W may be a carboxylic acid, a protected carboxylic acid, an active ester, an amine or a protected amine. Furthermore, W may be selected from the groups described above for Z. As discussed herein, the third functional group may be chemically orthogonal to one or both of the first functional groups.

Embodiments of the foregoing include but are not limited to:

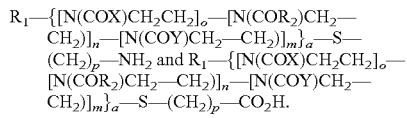

In an alternate embodiment, Z lacks the third functional group and is represented by the structure —S-T-V, wherein S is a sulphur atom, T is a linking group and V is an inert group. In this embodiment, representative T groups include alkylene groups. In a particular embodiment, T is —$(CH_2)_p$— where p is an integer selected from 1 to 10. V may be any inert group. In a particular embodiment, V is —$CO_2CH_3$ or —$C_6H_5$.

Embodiments of the foregoing include but are not limited to:

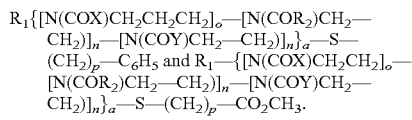

In still another alternate embodiment, the heterofunctional polyoxazoline derivatives are defined by the general structure:

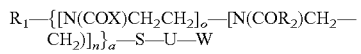

wherein:
$R_1$, X, $R_2$, o, n and a are as defined above;
S is a sulphur atom;
U is a linking group; and
W is the third functional group.

In this embodiment, representative U groups include alkylene groups. In a particular embodiment, U is —$(CH_2)_p$— where p is an integer selected from 1 to 10. In this embodiment, the second functional group is lacking. In these embodiments, Z contains a third functional group and the third functional group is chemically orthogonal to the first functional group on X. The first functional group may be selected from the groups described above. The third functional group W may be selected from the groups described above for X. In a particular embodiment, W may be a carboxylic acid, a protected carboxylic acid, an active ester, an amine or a protected amine.

Embodiments of the foregoing include but are not limited to:

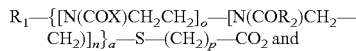

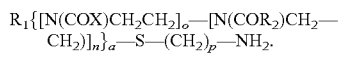

These heterofunctional polyoxazoline derivatives described herein may be prepared by terminating the POZ cation with a mercapto-ester (such as —S—$CH_2CH_2$—$CO_2CH_3$) or mercapto-protected amine (such as —S—$CH_2CH_2$—NH-tBoc). These heterofunctional polyoxazoline derivatives provide for effective, large-scale purification by ion-exchange chromatography (to remove secondary amines), and they provide chemically orthogonal functional groups X and W (—$CO_2H$ or —$NH_2$) for attachment of one or more target molecules, such as targeting, diagnostic or therapeutic moieties.

Multi-Arm Heterofunctional Polyoxazoline Derivatives

The present disclosure also provides for multi-armed heterofunctional polyoxazoline derivatives. The multi-armed heterofunctional polyoxazoline derivatives may contain from 2 to 8 polyoxazoline chains. In a particular embodiment, the multi-armed heterofunctional polyoxazoline derivatives contain 2 or 4 polyoxazoline chains. The multi-armed heterofunctional polyoxazoline derivatives may be represented by the general formula:

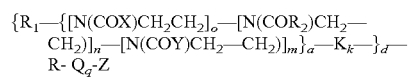

wherein:
$R_1$ is an initiating group;
$R_2$ lacks a functional group and is independently selected for each polyoxazoline chain from a substituted or unsubstituted alkyl, a substituted or unsubstituted alkenyl, a substituted or unsubstituted aralkyl or a substituted or unsubstituted heterocyclylalkyl group;
X is a pendent moiety bearing a first functional group;
Y is a pendent moiety bearing a second functional group;
K is a linking moiety linking each polyoxazoline chain to a branching moiety R;
Q is a linking moiety linking the branching moiety R to Z;
R is a branching moiety capable of forming linkages with Z, either directly or through linking group Q, and with each polyoxazoline chain, either directly or through the linking group K;
Z is a moiety containing a third functional group or an inert group;
A is independently selected for each polyoxazoline chain from ran which indicates a random copolymer or block which indicates a block copolymer;
d is an integer selected from 2-8;
k is an integer independently selected for each polyoxazoline chain from one or zero;
q is an integer selected from one or zero;
o is an integer independently selected for each polyoxazoline chain from 1-50;
m is an integer independently selected for each polyoxazoline chain from 0-50;
n is an integer independently selected for each polyoxazoline chain from 0-1000; and
wherein at least two of the first, second and third functional groups may be chemically orthogonal to one another.

In the general structure above, each POZ chain may be the same or may be different. Furthermore, the pendent moieties X and Y may be the same or may be different for each POZ chain.

Exemplary $R_1$ groups include, but not limited to, hydrogen, alkyl, substituted alkyl, aralkyl, or substituted aralkyl groups. In a particular embodiment, the initiating group is a methyl group. The $R_1$ group is selected to lack a functional group. Additional exemplary initiating groups are disclosed in PCT Application No. PCT/US2008/078159, which is hereby incorporated by reference for such teaching.

As shown by the general structure above, the heterofunctional polyoxazoline derivative comprises at least two functional groups. The first and second functional groups are present on the pendent moieties X and Y, respectively. In certain embodiment, a third functional group is present on the Z group; however, the presence of the third functional group is optional and in some embodiments Z may be inert (i.e., lacking the third functional group).

X and Y are pendent moieties bearing first and second functional groups, respectively. In certain embodiments, X and Y may contain a linking portion that links the first and second functional groups to the polyoxazoline derivative. Exemplary linking portions include alkylene groups. In certain cases, the alkylene group is a $C_1$-$C_{15}$ alkylene group. The linking portions of X and Y may be the same or may be different. For example, both X and Y may contain a $C_5$ alkylene group as the linking portion or X may contain a $C_5$ alkylene group as the linking portion and Y may contain a $C_8$ alkylene group as the linking portion.

Z may contain a third functional group or be inert. In those embodiments where Z contains a third functional group, the third functional group may be chemically orthogonal to one or both of the first and second functional groups.

The first, second and third functional groups include, but are not limited to, alkyne, amine, oxyamine, aldehyde, ketone, acetal, ketal, maleimide, ester, carboxylic acid, activated carboxylic acid (such as, but not limited to, N-hydroxysuccinimidyl (NHS) and 1-benzotriazineyl active ester), an active carbonate, a chloroformate, alcohol, azide, vinyl sulfone, or orthopyridyl disulfide (OPSS), provided that the selection is made so that at least two of the first, second and third functional groups are chemically orthogonal to one another.

Q is optional and can be any group capable of forming linkages with both the R and Z and will be different depending on the chemistry of the R and Z. Representative Q groups include, but are not limited to, substituted and unsubstituted alkylene groups. In a specific embodiment, Q is —$(CH_2)_p$—, where p is independently selected from 1-10.

K is optional and can be any group capable of forming linkages with both the POZ chain and R and will be different depending on the chemistry of the POZ chain and R. Representative K groups include substituted and unsubstituted alkyl, alkenyl or alkynyl groups. In a specific embodiment, K is —$(CH_2)_pO$—, —$(CH_2)_p$—CO—, —S—$(CH_2)_p$CONH—, —S—$(CH_2)_p$CO, —$(CH_2)_p$—NHCSO—, —$(CH_2)_p$—NHCO_2—, —NH—$(CH_2)_p$, or —NHCO_2—, where p is an integer from 0-10. K may be the same or different for each POZ chain.

R is a branching moiety capable of forming linkages with both POZ chains and Z, either directly or through linking groups K and Q, respectively. R may be selected from a nitrogen, an aryl group, or —$CR_3$—, where $R_3$ is hydrogen or a substituted or unsubstituted alkyl, a substituted or unsubstituted alkenyl, or a substituted or unsubstituted aralkyl group. In a specific embodiment, R is —NH—CH—$(CH_2)_3$—$CH_2$—NH— or —$(CH_2)_4$—CH—CO—NH—$(CH_2)_4$—CH—NH—CO—CH—$(CH_2)_4$—.

In the general structure above, at least two of the first, second and third functional groups must be present. Therefore, when m or n is 0 for each POZ chain, Z cannot be inert.

Several embodiments of the multi-aimed heterofunctional polyoxazoline derivative falling under the general structure above are presented below.

Example 1

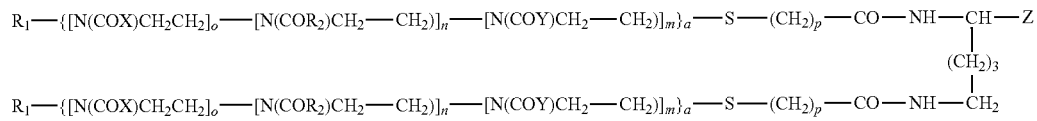

In this example, d is 2, k is 1, K is —S—$(CH_2)_p$—CO—, where p is an integer from 1-10, for each polyoxazoline chain, q is 0, R is NH—CH—$(CH_2)_3$—$CH_2$—NH and the first and second functional groups are chemically orthogonal to one another; Z may be chemically orthogonal to one or both of the first and second functional groups.

Example 2

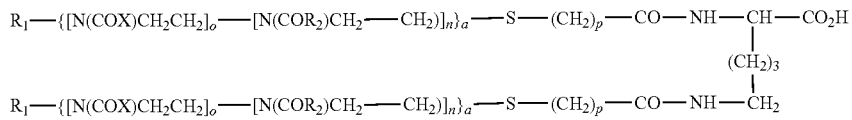

In this example, d is 2, k is 1, K is —S—$(CH_2)_p$—CO—, where p is an integer from 1-10, for each polyoxazoline chain, q is 0, R is NH—CH—$(CH_2)_3$—$CH_2$—NH, m is 0, Z is $CO_2H$ and the first and third functional groups may be chemically orthogonal to one another.

Example 3

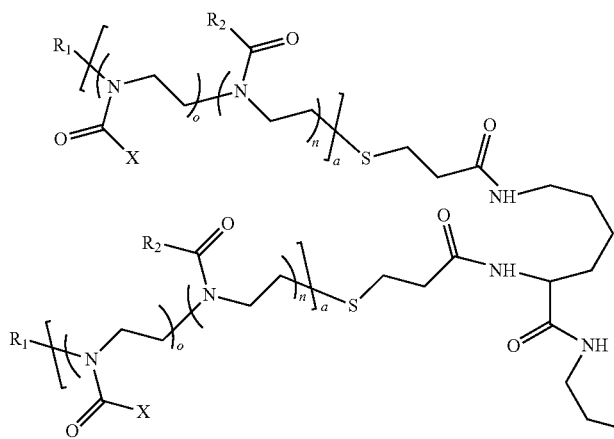

In this example, d is 4, k is 1 and K is —S—(CH$_2$)$_2$—CO—NH for each polyoxazoline chain, q and m are 0, R is —(CH$_2$)$_4$—CH—CO—NH—CO—(CH$_2$)$_4$—CH—NH—CO—CH—(CH$_2$)$_4$— and the first and third functional groups may be chemically orthogonal to one another.

Example 4

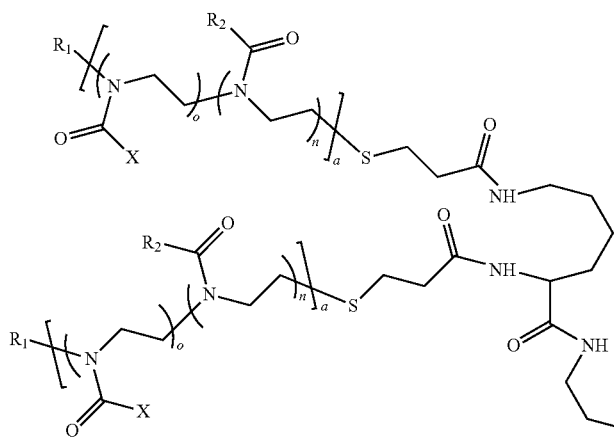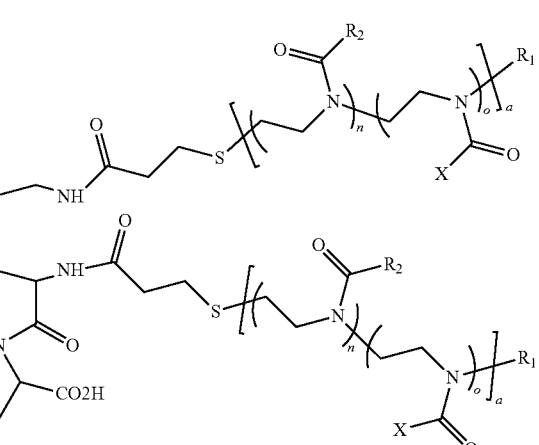

In this example, d, k, K, q, m and R are as in Example 3 and Z is CO$_2$H and the first and third functional groups may be chemically orthogonal to one another.

In all of the above embodiments, the polyoxazoline polymers contained in the heterofunctional polyoxazoline derivatives may be random or block copolymers. As used herein, a block copolymer includes those copolymers that have block configurations separated by a random copolymer sequence. Such random and block copolymers may be produced by controlling the introduction of various intermediates during the synthesis process as described below.

Furthermore, in all the embodiments discussed above, one or more of the functional groups may be charged species. For example, one or more of the functional groups may be a carboxylic acid having a negative charge or an amine having a positive charge. As such, the functional groups may form ionic linkages with one or more target molecules.

Methods of Synthesis

In one embodiment, the polymers of the present disclosure are prepared by co-polymerization of appropriate 2-substituted-2-oxazolines containing functional groups. For example, preparation of a water-soluble co-polymer bearing alkyne groups and acetal groups, in addition to a simple 2-alkyl-2-oxazoline can be synthesized using the following oxazoline monomers:

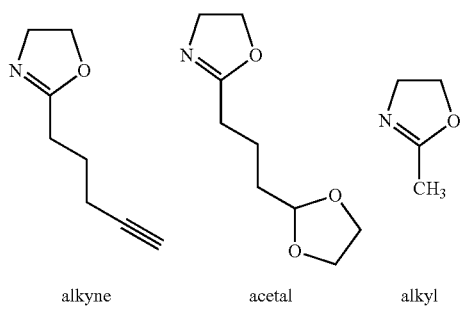

alkyne     acetal     alkyl

The polymerization is initiated by an electrophile such as, but not limited to, methyl triflate, methyl tosylate, p-toluene-sulfonic acid, or triflic acid. The co-polymerization can be terminated by a nucleophilic reagent as discussed herein. If terminal functionality is desired, a functionalized terminating agent, such as but not limited to, methyl thiolacetate can be used. For a non-reactive termination terminus, a nucleophile such as an alkyl mercaptan can be used. Similarly a terminating hydroxyl group is also unreactive to many reagents and can therefore be useful in this application. Preferred solvents for the polymerization are chlorobenzene or acetonitrile. The preferred temperature range is from about 40° C. to about 120° C. The time required for the polymerization is dependent on the temperature, the desired molecular weight, and the solvent and can range from about 1 h to about 100 h. In certain embodiments, it is desirable to limit the polymerization reaction to the time required to substantially complete the polymerization reaction. In one embodiment, the progress of the polymerization reaction is monitored using MALDI and/or GPC.

The polymerization can be conducted in several ways. In one embodiment, a mixture of the appropriate oxazoline components can be reacted with the initiator in a preferred solvent with stirring. This reaction yields a random copolymer when the oxazoline components are equally reactive with one another or a block copolymer when one or more of the oxazoline components are less reactive towards one another. In an alternate embodiment, the polymer may also be synthesized in blocks by initiating polymerization with an appropriate initiator in a preferred solvent using only one oxazoline component. The reaction may be monitored with MALDI or GPC to determine when the reaction is substantially complete. When polymerization of the first block is complete, a second oxazoline component is added to reinitiate the polymerization with the incipient living cation at the terminus of the polymer chain; monitoring of the polymerization reaction may be carried out as described. The solvent may be the same as in the first polymerization reaction or different; the reaction temperature and other variables may also be adjusted as desired. Upon completion of the polymerization of the second block, a third oxazoline component is added to reinitiate the polymerization with the living cation at the terminus of the polymer chain; monitoring of the polymerization reaction may be carried out as described. The solvent may be the same as in the first or second polymerization reactions or different; the reaction temperature and other variables may also be adjusted as desired. When the third polymerization step is completed, the polymerization may be terminated by the addition of a terminating agent. The oxazoline components may contain functional groups, or may lack a functional group. The sequential polymerizations can be done in any order. In another embodiment, random copolymerization of two of the oxazoline monomers, followed by continued polymerization of a third block can also be done to produce a polymer having both random and block configurations. In one embodiment, one of the oxazoline monomers lacks a functional group.

Once the desired polymerization process is completed, the polymer is precipitated, such as in ethyl ether, several times and dried under vacuum. The polymer may be further characterized by standard techniques such as but not limited to MALDI, NMR, and GPC.

Work with polyethylene glycol has shown that it is frequently necessary in modification of target molecules to utilize polymers of molecular weights (MWs) of 20,000 Da or higher and molecular weight distributions, or polydispersities (PDs), of less than 1.1. There has been a great deal of work showing that MWs and PDs in the above range cannot be achieved for POZ chains with conventional techniques. As is known in the art PD values will vary with MW; in general, as the molecular weight increases the PD value also increases. It is generally seen that as the molecular weight of growing POZ chains reaches approximately 5,000 Da, the polydispersity increases appreciably. Side reactions, including, but not limited to, chain transfer, begin to grow in importance. The prior art techniques described above when used to generate POZ chains of high MW produce POZ derivatives with unacceptable PD values. The polyoxazoline derivatives of the present disclosure may be produced using polyoxazoline chains that are manufactured using novel methods that result in polyoxazoline derivatives with low PD values and a decreased amount of impurities produced by unwanted side reactions, such as, but not limited to, chain transfer. In one embodiment, the polyoxazoline chains are manufactured to minimize unwanted side reactions, such as, but not limited to, chain transfer, allowing the production of POZ derivatives of increased purity with low PD values. Therefore, the POZ derivatives of the present disclosure may be produced with increased purity and with low PD values suitable for use in pharmaceutical applications. Such methods are described in PCT Application No. PCT/US2008/078159, which is hereby incorproated by reference for such teaching.

Use of the Heterofunctional Polyoxazoline Derivatives

The heterofunctional polyoxazoline derivatives of the present disclosure possess two or more chemically orthogonal functional groups and thus allow for attachment of two or more different target molecules to the polymer.

The novel heterofunctional polyoxazoline derivatives prepared as described above are intended for formation of conjugates with various target molecules, such as, but not limited to, therapeutic, diagnostic and targeting moieties. Target molecules include, but are not limited to, polypeptides such as, but not limited to, interferons (including alpha, beta and gamma), growth hormone, interleukins, enzymes, antibodies (including antibody fragments and monoclonal antibodies), blood factors (including GCSF, erythropoietin, and Factor VIII) and insulin. In addition, it is intended that the POZ derivatives of the current disclosure be coupled to carbohydrates, oligonucleotides and small-molecule therapeutics.

The heterofunctional polyoxazoline derivatives of the present disclosure, possessing functional groups that have orthogonal chemistries, are ideally suited for preparation of polyoxazoline derivatives linked to target molecules with distinct functions. Such an approach is possible due to the presence of two or more functional groups on the polyoxazoline derivative that are chemically orthogonal to one another. As a result, target molecules with different linkage chemistries can be incorporated into the polyoxazoline derivative in a controlled, directed manner. Such an approach is capable of producing targeted polyoxazoline therapeutic and/or diagnostic conjugates. Exemplary active groups, binding partners on target molecules and linkages formed there between are disclosed in PCT Application No. PCT/US2008/078159, which is hereby incorporated by reference for such teaching.

In one embodiment, the target molecule may a therapeutic and/or diagnostic agent and a targeting agent. The linkages to the target molecule may be hydrolytically stable or hydrolytically unstable or a combination thereof. However, in one embodiment, all linkages in the polyoxazoline derivative itself are hydrolytically stable. For example, an ester linkage to a target molecule would be hydrolytically unstable in vivo, while an amide linkage would be stable for an extended period of time. The described polyoxazoline derivatives provide a wide range of options in linking target molecules to the described polymer structure. Depending on the number of functional groups present, the number of target molecules linked to the polyoxazoline derivative can be varied from 1 to at least 100.

M-PEOZ-OH and H-PEOZ-COOH samples of different molecular weights as determined by MALDI (750, 1K, 2K, 5K, 10K, 20K, 30K and 40K). MALDI-TOF MS was performed with a Bruker, Microflex™ machine using dithranol as matrix. NMR was performed on a Varian 500 MHz machine.

Example 1

Preparation of Random-Co-Polymer of with Two Pendent Groups

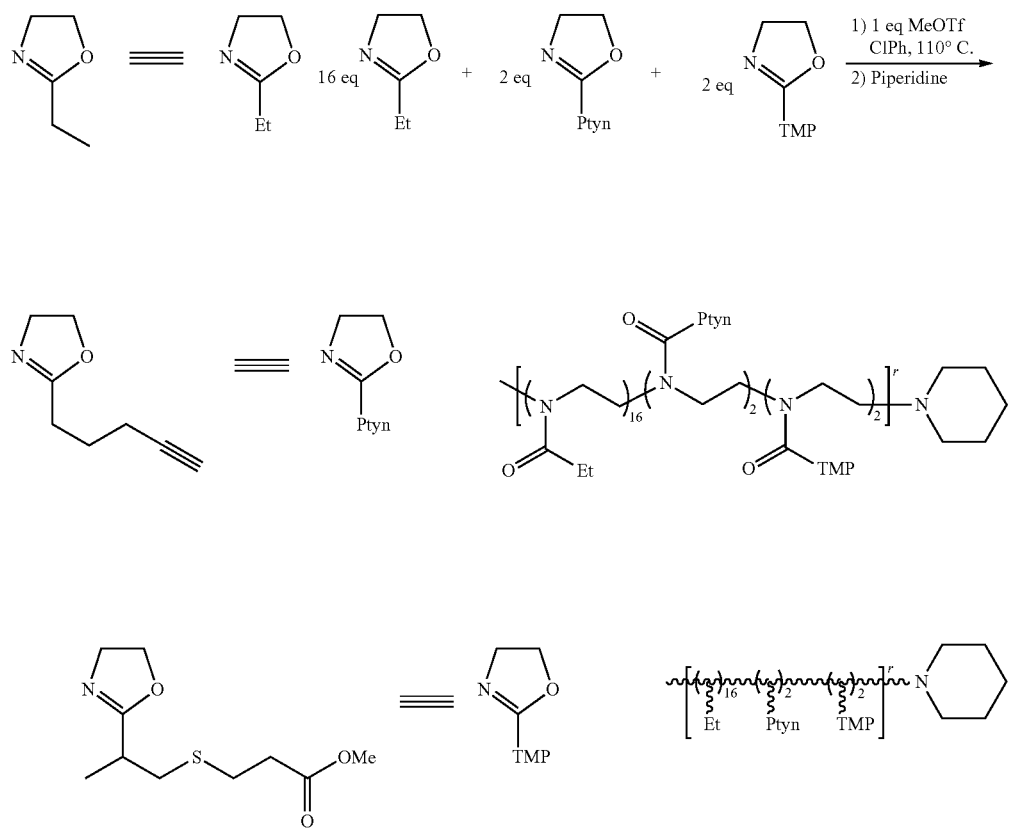

EXAMPLES

Reagents

Reagents were acquired from EM Science, Oakwood Products, Fluka, Calbiochem, Chevron Phillips Chemicals International, or Aldrich and distilled before use. Chlorobenzene and oxazolines were distilled from calcium hydride. GPC was performed on an Agilent Technologies machine with an 1100 quaternary pump and RI detector. Two Phenogel™ GPC columns (Phenomenex, 5μ, 500 A° and 1000 A°, 300×7.8 mm) were used in series in a column heater (60° C.). The mobile phase was 100% N,N'-dimethylformamide (DMF) at a flow rate of 1 mL/min. A calibration curve was generated with A solution of monomers comprising 2-(4-pentynyl)-2-oxazoline (PtynOZ—0.274 g, 0.002 mol), T-methyl propionate-2-oxazoline (TMPOZ—0.463 g, 0.002 mol), and 2-ethyl-2-oxazoline (EOZ—1.62 mL, 0.016 mol) was prepared in chlorobenzene (10 mL). To this solution was added methyl triflate (MeOTf—0.113 mL, 0.001 mol) at room temperature. After stirring for 30 minutes, the mixture was heated to 110° C. for 45 minutes. The mixture was cooled to 0° C. and then terminated using piperidine (0.30 mL, 0.003 mol). After stirring for 2 hours at room temperature, the mixture was dripped into diethyl ether, decanted, and dried in vacuo to give 2.4 g of a white powder in quantitative yield.

The product had a calculated Mn of 2400 Da and a Mn (as determined by GPC) of 2440 with a polydispersity index (PDI) of 1.14. The sample exhibited a high molecular weight shoulder of less than 3%. $^1$H NMR spectra showed peaks corresponding to pendent groups (acetylene and methyl ester) in the proper ratio.

Example 2

Preparation of Block-Co-Sol Mer Via Stepwise Addition of Monomer and Monomer Mixtures

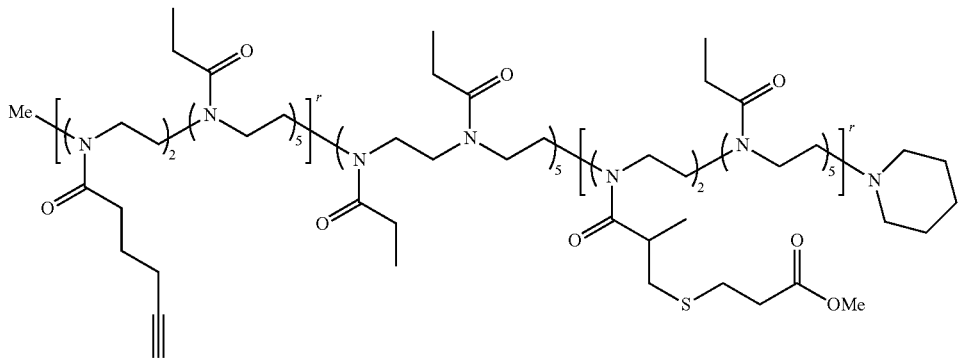

To a solution of PtynOZ (0.274 g, 0.002 mol, 2 eq) in chlorobenzene (7.5 mL) was added MeOTf (0.113 mL, 0.001 mol, 1 eq) at room temperature. The mixture was stirred for 15 minutes and then ethyl oxazoline (EOZ, 0.5 mL, 0.005 mol, 5 eq) was added. The mixture was heated to 110° C. and stirred for 17 minutes. To introduce the second block (homopolymer of EOZ), EOZ (1.01 mL, 0.01 mol, 10 eq) was added and the resulting mixture was stirred for 10 minutes at 110° C. The third block was introduced by the addition of a solution of T-methyl propionate oxazoline (TMPOZ, 0.463 g, 0.002 mol, 2 eq) and EOZ (0.5 mL, 0.005 mol, 5 eq). After stirring for 10 minutes at 110° C., the mixture was cooled to room temperature using an ice/water bath and terminated by the addition of piperidine (0.4 mL, 0.004 mol). The resulting mixture was allowed to stir overnight, and precipitated by addition to diethyl ether. The solution was decanted and the remaining material was dried in vacuo to give 1.8 g of the desired product as a white powder in 67% yield.

$^1$H NMR (Varian, 500 MHz, 10 mg/mL CDCl$_3$) showed the usual backbone peaks at 1.12 ppm (m, 3H, CH$_3$CH$_2$CO—); 2.30 ppm (m) and 2.41 (s) (total area 2H, CH$_3$CH$_2$CO—); and 3.46 ppm (m, 4H, —NCH$_2$CH$_2$N—). The pentynyl pendant group peaks appear at 1.86 ppm (m, 2H, —CH$_2$CH$_2$C≡CH), 1.98 ppm (s, 1H, —CH$_2$CH$_2$C≡CH), and 2.04 ppm (br s, 1H, —CH$_2$CH$_2$C≡CH). The TMP pendent group peaks show at 2.60-2.88 ppm (m, 7H, —C(=O)CH(CH$_3$)CH$_2$SCH$_2$CH$_2$CO$_2$Me) and 3.67 ppm (s, 3H, CH$_2$CO$_2$Me). The ratio of Ptyn, TMP, and EOZ was determined as 2:1.7:20. GPC gave Mn=2510 Da with PDI of 1.14. MALDI provided Mn=2725 with PDI of 1.04.

Example 3

Synthesis of Random H-(Ptyn)$_4$(EOZ)$_{20}$-T-CO$_2$H

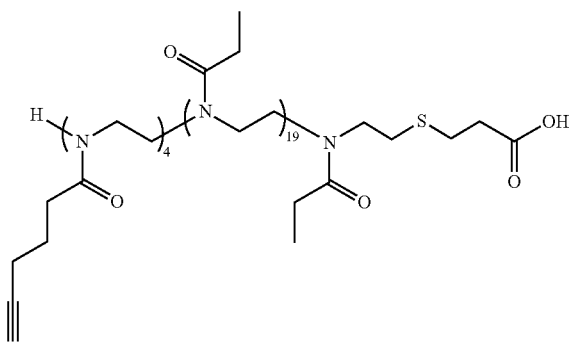

Triflic acid (HOTf, 0.177 mL, 0.002 mol) was added into a solution of 2-pentynyl-2-oxazoline (PtynOZ, 1.097 g, 0.008 mol, 4 eq) and 2-ethyl-2-oxazoline (EOZ, 4.04 mL, 0.04 mol, 20 eq) in chlorobenzene (20 mL). After stirring for 5 minutes at room temperature, the mixture was heated to 110° C. for 30 minutes followed by cooling to room temperature using an ice/water bath. In a separate flask, the terminating reagent was prepared by the dropwise addition of methyl 3-mercaptopropionate (0.87 mL, 0.008 mol) into a suspension of sodium hydride (60% in mineral oil, 0.24 g, 0.006 mol) in chlorobenzene (60 mL), at room temperature. This mixture was stirred for 2 hours, before the solution of H-(Ptyn)$_4$(EOZ)$_{20}{}^+$ in chlorobenzene was slowly added. The resulting mixture was then stirred for 18 hours at room temperature. The organic solvent was evaporated with a rotary evaporator and the white residue was dissolved in water and the pH was adjusted to 12.0. After stirring for 1 hour, the mixture was acidified (pH ~3) and purified by ion-exchange chromatography using SP Sepharose FF and DEAE Sepharose FF to give the desired product as a white powder (yield was 2.2 g, 42%).

$^1$H NMR (Varian, 500 MHz, 10 mg/mL CDCl$_3$) showed the usual backbone peaks at 1.13 ppm (m, 3H, CH$_3$CH$_2$CO—); 2.32 ppm (m) and 2.41 (s) (total area 2H, CH$_3$CH$_2$CO—); and 3.47 ppm (m, 4H, —NCH$_2$CH$_2$N—). The terminal group peaks appear at 2.63 ppm (m, 2H, —SCH$_2$CH$_2$CO$_2$H), 2.74 ppm (m, 2H, —CH$_2$SCH$_2$CH$_2$CO$_2$H), and 2.85 ppm (m, 2H, —SCH$_2$CH$_2$CO$_2$H). The pendent pentynyl group peaks appear at 1.85 ppm (m, 2H, —CH$_2$CH$_2$C≡CH) and 2.03 ppm (br s, 1H, —CH$_2$CH$_2$C≡CH). The ratio of Ptyn and EOZ was 4:20. GPC gave Mn=3100 Da and Mp=3140 Da with PDI of 1.05. MALDI provided Mn=2900 Da with PDI of 1.03.

Example 4

Synthesis of Random H-(Ptyn)$_4$(EOZ)$_{20}$-T-NH$_2$

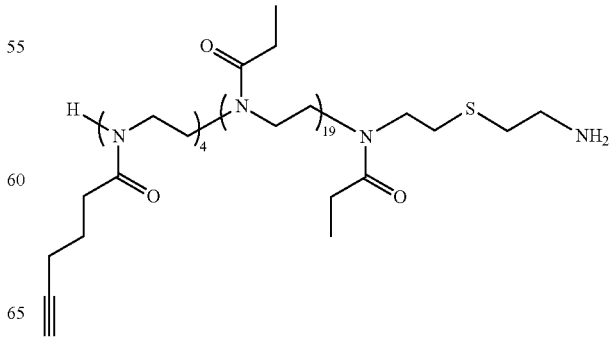

Triflic acid (HOTf, 0.177 mL, 0.002 mol) was added into a solution of 2-pentynyl-2-oxazoline (PtynOZ, 1.097 g, 0.008 mol, 4 eq) and 2-ethyl-2-oxazoline (EOZ, 4.04 mL, 0.04 mol, 20 eq) in chlorobenzene (20 mL). After stirring for 5 minutes at room temperature, the mixture was heated to 110° C. for 30 minutes followed by cooling to room temperature using an ice/water bath. In a separate flask, the terminating reagent was prepared by the dropwise addition of N-Boc cysteamine (1.01 mL, 0.006 mol) into a suspension of sodium hydride (60% in mineral oil, 0.24 g, 0.006 mol) in chlorobenzene (60 mL), at room temperature. This mixture was stirred for 2 hours, before the solution of H-(Ptyn)$_4$(PEOZ)$_{20}$$^+$ in chlorobenzene was added dropwise. The resulting mixture was stirred for 18 hours at room temperature. Volatiles were removed using a rotary evaporator and the residue was dissolved in water. The pH of the solution was adjusted to 3.0. The resulting aqueous solution was passed through an Amberlite column and then an ion-exchange column using SP Sepharose FF. The aqueous solution was charged with NaCl (15% w/w) and extracted with dichloromethane. The combined organic phases were dried over anhydrous sodium sulfate, filtered, and concentrated using a rotary evaporator to provide 4.73 g of H-(Ptyn)$_4$(EOZ)$_{20}$-T-NHBoc as a white powder in 87% yield.

$^1$H NMR (Varian, 500 MHz, 10 mg/mL CDCl$_3$) showed the usual backbone peaks at 1.12 ppm (m, 3H, CH$_3$CH$_2$CO—); 2.28 ppm (m) and 2.41 (s) (total area 2H, CH$_3$CH$_2$CO—); and 3.47 ppm (m, 4H, —NCH$_2$CH$_2$N—). The terminal group peaks appear at 1.44 ppm (s, 9H, —NHBoc), 2.63 ppm (m, 2H, —SCH$_2$CH$_2$NHBoc), 2.71 ppm (m, 2H, —CH$_2$SCH$_2$CH$_2$NHBoc), and 3.30 ppm (m, 2H, —SCH$_2$CH$_2$NHBoc). The pendent group peaks show at 1.84 ppm (m, 2H, —CH$_2$CH$_2$C≡CH) and 2.04 ppm (br s, 1H, —CH$_2$CH$_2$C≡CH). The ratio of Ptyn and EOZ was determined to be 4:20. GPC gave Mn=3900 Da and Mp=4505 Da with PDI of 1.07.

H-(Ptyn)$_4$(EOZ)$_{20}$-T-NHBoc (4.4 g) was dissolved in 3N methanolic HCl and then stirred for 1 hour at room temperature. Most of volatiles were removed using a rotary evaporator and the residue was dissolved in water and the pH adjusted to ~12.5. The aqueous solution was charged with NaCl (15% w/w) and extracted with dichloromethane. The combined organic phases were dried over sodium sulfate, filtered, and concentrated using a rotary evaporator to provide 3.9 g of H-(Ptyn)$_4$(EOZ)$_{20}$-T-NH$_2$ as a white powder. Deprotection of —NHBoc was confirmed by AKTA prime on SP Sepharose FF column media and by $^1$H NMR spectra showing the disappearance of -Boc group peak at 1.44 ppm and the shifting of —CH$_2$NH$_2$ from 3.30 ppm to 2.92 ppm. In addition, the comparison of integration shows that the polymer contains four pendent groups. GPC gave Mn=3067 Da and Mp=3927 Da with PDI of 1.16.

Example 5

Synthesis of Random H-(NHBoc)$_4$(EOZ)$_{20}$-T-CO$_2$H

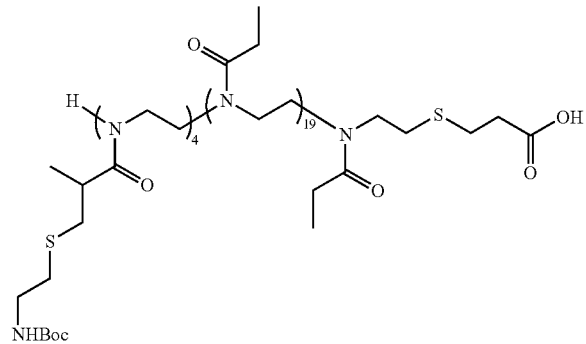

Triflic acid (HOTf, 0.177 mL, 0.002 mol) was added into a solution of T-NHBoc-2-oxazoline (NHBocOZ, 1.097 g, 0.008 mol, 4 eq) and 2-ethyl-2-oxazoline (EOZ, 4.04 mL, 0.04 mol, 20 eq) in chlorobenzene (20 mL). After stirring for 5 minutes at room temperature, the mixture was heated to 110° C. for 30 minutes followed by cooling to room temperature using an ice/water bath. In a separate flask, the terminating reagent was prepared by the dropwise addition of methyl 3-mercaptopropionate (0.87 mL, 0.008 mol) into a suspension of sodium hydride (60% in mineral oil, 0.24 g, 0.006 mol) in chlorobenzene (60 mL) at room temperature. This mixture was stirred for 2 hours before the solution of H-(NHBoc)$_4$(EOZ)$_{20}$$^+$ in chlorobenzene was slowly added into it. The resulting mixture was stirred for 18 hours at room temperature. The organic solvent and other volatiles were removed using a rotary evaporator and the residue was dissolved in water and the pH of this aqueous solution was adjusted to 12.0. After stirring for 1 hour, the mixture was acidified (pH ~3) and purified by ion-exchange chromatography using SP Sepharose FF and DEAE Sepharose FF to give the desired product as a white powder (yield was 1.4 g, 22%).

$^1$H NMR (Varian, 500 MHz, 10 mg/mL CDCl$_3$) showed the usual backbone peaks at 1.13 ppm (m, 3H, CH$_3$CH$_2$CO—); 2.31 ppm (m) and 2.41 (s) (total area 2H, CH$_3$CH$_2$CO—); and 3.47 ppm (m, 4H, —NCH$_2$CH$_2$N—). The terminal group peaks appear at 2.63 ppm (m, 2H, —SCH$_2$CH$_2$CO$_2$H), 2.73 ppm (m, 2H, —CH$_2$SCH$_2$CH$_2$CO$_2$H), and 2.84 ppm (m, 2H, —SCH$_2$CH$_2$CO$_2$H). The significant pendent group peaks show at 1.43 ppm (s, 9H, —NHBoc) and 3.28 ppm (m, 2H, —CH$_2$NHBoc). The ratio of NHBoc and EOZ was determined as 4:20. GPC gave Mn=3760 Da and Mp=3550 Da with PDI of 1.09. MALDI provided Mn=3130 with PDI of 1.03.

Example 6

Synthesis of Random H-(TPA)$_4$(EOZ)$_{20}$-T-NHBoc

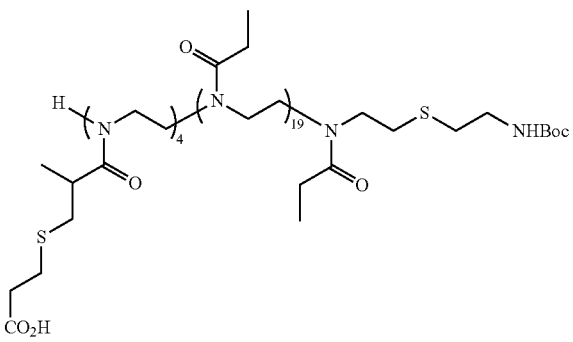

Triflic acid (HOTf, 0.177 mL, 0.002 mol) was added into a solution of T-methyl propionate-2-oxazoline (TMPOZ, 1.85 g, 0.008 mol, 4 eq) and 2-ethyl-2-oxazoline (EOZ, 4.04 mL, 0.04 mol, 20 eq) in chlorobenzene (20 mL). After stirring for 5 minutes at room temperature, the mixture was heated to 110° C. for 30 minutes followed by cooling to room temperature using an ice/water bath. In a separate flask, the terminating reagent was prepared by the dropwise addition of N-Boc cysteamine (1.01 mL, 0.006 mol) into a suspension of sodium hydride (60% in mineral oil, 0.24 g, 0.006 mol) in chlorobenzene (60 mL) at room temperature. The mixture was stirred for 2 hours, and the solution of H-(TMP)$_4$(EOZ)$_{20}$$^+$ in chlorobenzene was then slowly added into it. The resulting mixture was stirred for 18 hours at room temperature. The volatiles were then removed using a rotary evaporator and the residue was dissolved in water (pH ~3). The resulting aqueous solution was passed through an Amberlite column and then an ion-exchange column with SP Sepharose FF media. The aqueous solution was charged with NaCl (15% w/w) and extracted with dichloromethane. The combined organic phases were dried over sodium sulfate, filtered, and concentrated using a rotary evaporator to provide 4.8 g of H-(TMP)$_4$(EOZ)$_{20}$-T-NHBoc as a white powder (78% yield).

$^1$H NMR (Varian, 500 MHz, 10 mg/mL CDCl$_3$) showed the usual backbone peaks at 1.12 ppm (m, 3H, CH$_3$CH$_2$CO—); 2.30 ppm (m) and 2.41 (s) (total area 2H, CH$_3$CH$_2$CO—); and 3.46 ppm (m, 4H, —NCH$_2$CH$_2$N—). The terminal group peaks appear at 1.44 ppm (s, 9H, —NHBoc), 2.61 ppm (m, 2H, —SCH$_2$CH$_2$NHBoc), 2.79 ppm (m, 2H, —CH$_2$SCH$_2$CH$_2$NHBoc), and 3.31 ppm (m, 2H, —SCH$_2$CH$_2$NHBoc). The pendent group peaks show at 2.60-2.90 ppm (m, 7H, —C(=O)CH(CH$_3$)CH$_2$SCH$_2$CH$_2$CO$_2$Me) and 3.67 ppm (s, 3H, CH$_2$CO$_2$Me). The ratio of TMP and EOZ was determined as 3.3:20. GPC gave Mn=2340 Da and Mp=2200 Da with PDI of 1.08.

H-(TMP)$_4$(EOZ)$_{20}$-T-NHBoc (4.4 g) was dissolved in water and the pH adjusted to ~12.5. After stirring for 1 hour at room temperature, purification was performed by ion-exchange chromatography using DEAE Sepharose FF. The aqueous solution was charged with NaCl (15% w/w) and extracted with dichloromethane. The combined organic phases were dried over anhydrous sodium sulfate, filtered, and concentrated using a rotary evaporator to provide 2.0 g of H-(TPA)$_4$(EOZ)$_{20}$-T-NHBoc as a white powder in 32% yield. Hydrolysis of —CO$_2$Me was confirmed by AKTA prime on DEAE Sepharose FF and by $^1$H NMR spectra (disappearance of —CO$_2$Me group peak at 3.67 ppm).

Example 7

Synthesis of H-[(TPA)$_4$(EOZ)$_{20}$][(NHBoc)$_4$CEOZ)$_{20}$]-T-Bz minutes, the mixture was cooled to room temperature using an ice/water bath. The terminating reagent was prepared in a separate flask by the slow addition of benzyl mercaptan (0.35 mL, 0.003 mol) into a suspension of sodium hydride (60% in mineral oil, 0.08 g, 0.002 mol) in chlorobenzene (10 mL) at room temperature. After the mixture was stirred for 2 hours, the solution of living polymer species in chlorobenzene was added dropwise to the termination mixture. The resulting mixture was stirred for 18 hours at room temperature and then precipitated by addition to diethyl ether. The precipitated solution was filtered, and dried to give 4.8 g of polymer having methyl ester and —NHBoc as the pendent groups. The polymer was dissolved in water, passed through an Amberlite column and then an ion-exchange column with SP Sepharose FF packing. The resulting aqueous solution was charged with NaCl (15% w/w) and extracted with dichloromethane. The combined organic phases were dried over sodium sulfate, filtered, and concentrated to provide 3.72 g of H-[(TMP)$_4$(EOZ)$_{20}$][(NHBoc)$_4$(EOZ)$_{20}$]-T-Bz as a white powder in 78% yield.

$^1$H NMR (Varian, 500 MHz, 10 mg/mL CDCl$_3$) showed the usual backbone peaks at 1.12 ppm (m, 3H, CH$_3$CH$_2$CO—); 2.30 ppm (m) and 2.41 (s) (total area 2H, CH$_3$CH$_2$CO—); and 3.47 ppm (m, 4H, —NCH$_2$CH$_2$N—). The terminal group peaks appear at 2.56 ppm (m, 2H, —CH$_2$SCH$_2$Ar), 3.74 ppm (s, 2H, —SCH$_2$Ar), 7.27 ppm (m, 1H, —Ar), 7.34 ppm (m, 5H, —Ar). The TMP pendent group peaks show at 2.60-2.88 ppm (m, 7H, —C(=O)CH(CH$_3$)CH$_2$SCH$_2$CH$_2$CO$_2$Me) and 3.67 ppm (s, 3H, CH$_2$CO$_2$Me). The —NHBoc pendent group peaks show at 1.42 ppm (s, 9H, —NHBoc) and 3.28 ppm (m, 2H, —CH$_2$NHBoc). The ratio of TMP, NHBoc, and EOZ was determined as 3.5:2:40. GPC gave Mn=4050 Da and Mp=4690 Da with PDI of 1.16.

H—RTMP)$_4$(EOZ)$_{20}$][(NHBoc)$_4$(EOZ)$_{20}$]-T-Bz (0.8 g) was dissolved in water and the pH was adjusted to ~13.0 using 0.5 M NaOH solution. After stirring for 1 hour, the mixture was extracted with dichloromethane and the combined

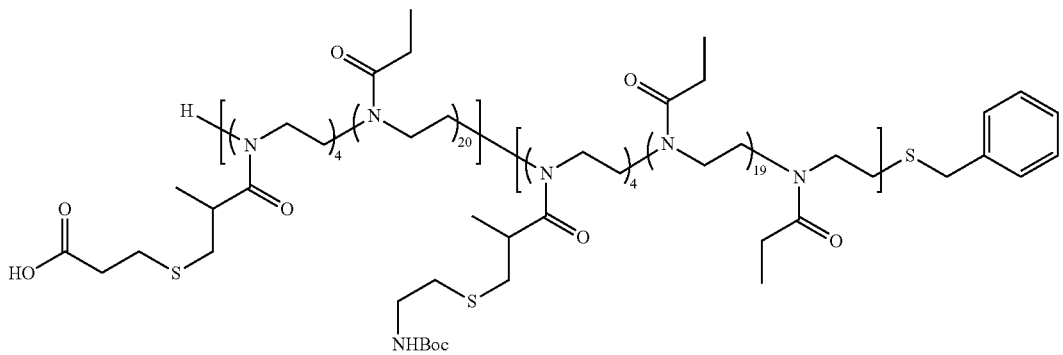

Triflic acid (HOTf, 88.5 μL, 0.001 mol) was added into a solution of T-methyl propionate-2-oxazoline (TMPOZ, 0.925 g, 0.004 mol, 4 eq) and 2-ethyl-2-oxazoline (EOZ, 2.02 mL, 0.02 mol, 20 eq) in chlorobenzene (12 mL). After stirring for 5 minutes at room temperature, the mixture was heated to 110° C. for 30 minutes and then a solution of T-NHBoc-2-oxazoline (NHBocOZ, 1.154 g, 0.004 mol, 4 eq) and 2-ethyl-2-oxazoline (EOZ, 2.02 mL, 0.02 mol, 20 eq) in chlorobenzene (12 mL) was added. After heating for an additional 30 organic phases were dried over sodium sulfate, filtered, and concentrated using a rotary evaporator. The resulting solution was precipitated by addition to diethyl ether. The diethyl ether solution was decanted and the remaining white powdery material was dried in vacuo to give the desired product, H-[(TPA)$_4$(EOZ)$_{20}$][(NHBoc)$_4$(EOZ)$_{20}$]-T-Bz in a quantitative yield. The hydrolysis was confirmed by ion exchange chromatography using a DEAE Sepharose FF. GFC and $^1$H NMR showed the hydrolysis of the —CO$_2$Me group.

Example 8

Synthesis of M-(PPtyn)$_2$(PEOZ)$_{18}$-T-CO$_2$H

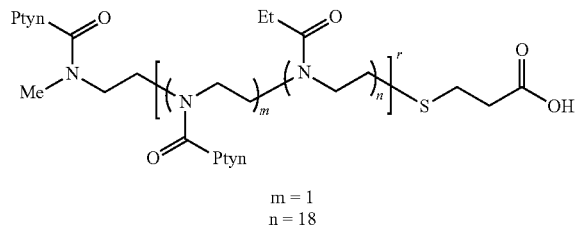

m = 1
n = 18

Methyl triflate (MeOTf, 0.556 mL, 0.005 mol) was added into a solution of 2-pentynyl-2-oxazoline (PtynOZ, 1.37 g, 0.01 mol, 2 eq) in chlorobenzene (20 mL). After stirring for 10 minutes at room temperature, 2-ethyl-2-oxazoline (9.09 mL, 0.09 mol, 18 eq) was added and the mixture was heated to 110° C. for 30 minutes followed by cooling to 0° C. To obtain a terminating reagent, methyl 3-mercaptopropionate (2.17 mL, 0.02 mol) was added dropwise into a suspension of potassium tert-butoxide (1.12 g, 0.01 mol) in chlorobenzene (10 mL) at 0° C. After the mixture was stirred for 2 hours in the cold, the solution of M-(PPtyn)(PEOZ)$^+$ in chlorobenzene was added dropwise. The mixture was stirred in the cold for 4 hours and then stirred for 18 hours at room temperature. Water (100 mL) was added and the mixture was acidified (pH ~3) by the addition of 5% aqueous HCl solution. Most of volatiles including chlorobenzene were removed using rotary evaporation. The resulting aqueous solution was treated with NaOH (1.0 g, 0.025 mol). After stirring for 1 hour, the mixture was acidified with 5% aqueous HCl solution and then extracted with dichloromethane. The combined organic phases were dried over sodium sulfate, filtered, concentrated, and precipitated by addition to ether. The ether was decanted and the residue was dried under vacuum. GFC showed that the crude product contains hydroxyl-terminated polymer (20%) and the desired acid-terminated polymer (80%). Further purification was performed by ion-exchange chromatography using DEAE Sepharose FF to give 5.6 g of the product in 61% yield. NMR (Varian, 500 MHz, 10 mg/mL CDCl$_3$) shows peaks for pendant pentynyl group at 1.85 ppm (m, 2H, —CH$_2$CH$_2$C≡CH); and 1.98 ppm (m, 1H, —CH$_2$CH$_2$C≡CH). GPC and GFC show a single main peak, with Mn 1830 Da and PD of 1.10.

Example 9

Synthesis of {M-(PPtyn)$_2$(PEOZ)$_{18}$}$_2$-Lys-CO$_2$H

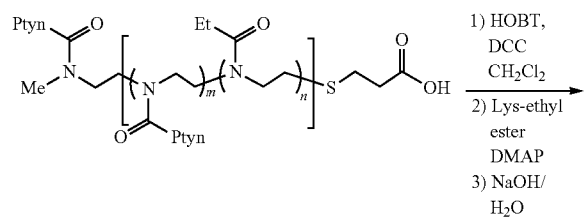

A solution of M-(PPtyn)$_2$(PEOZ)$_{18}$-T-CO$_2$H (Mn=1830 Da, 2.0 g, 1.09 mmol) and 1-HOBT (0.351 g, 2.60 mmol) in acetonitrile (40 mL) was concentrated by rotary evaporation to dry azeotropically. The residue was dissolved in dry CH$_2$Cl$_2$ (20 mL) and then DCC (0.322 g, 1.56 mmol) was added. After the mixture was stirred for 3 hours at room temperature, L-lysine ethyl ester dihydrochloride (0.129 g, 0.520 mmol) and DMAP (0.318 g, 2.60 mmol) were added. After stirring for 18 hours at room temperature, the mixture was added to ether (150 mL) to give a white precipitate. The compound was filtered and dried under vacuum to give {M-(PPtyn)$_2$(PEOZ)$_{18}$}$_2$-Lys-ethyl ester as a white powder. GPC and GFC showed the mixture of main product (98%, Mn=4540 Da, PD=1.04) and excess of acid polymer (2. The crude product was passed through a DEAE Sepharose FF column to remove the excess amount of acid polymer. The resulting aqueous solution was treated with NaOH (0.104 g, 2.60 mmol) for 1 hour. The mixture was acidified with 5% aqueous HCl solution and then extracted with dichloromethane. The combined organic phases were dried over sodium sulfate, filtered, concentrated, and precipitated by addition to ether. The ether was decanted and the residue was dried under vacuum to give 2.0 g of a white powder in 92% yield. $^1$H NMR showed the completion of hydrolysis according to the disappearance of ethyl group peaks and peaks for lysine core at 1.42 ppm (br s, 2H, —C(=O)NHCH$_2$CH$_2$CH$_2$—); 1.54 ppm (br s, 2H, —C(=O)NHCH$_2$CH$_2$—); 1.85 ppm (m, 2H, —CH$_2$CH(CO$_2$H)NH—); and 4.52 ppm (m, 1H, —CH$_2$CH(CO$_2$H)NH—). MALDI provided Mn=4240 Da with PD of 1.01.

Example 10

Synthesis of {M-(PPtyn)(PEOZ)}$_2$Lys-NHS

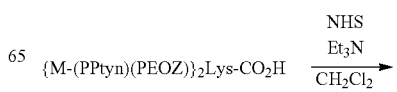

{M-(PPtyn)(PEOZ)}$_2$Lys-CO$_2$H $\xrightarrow[CH_2Cl_2]{NHS \\ Et_3N}$

-continued

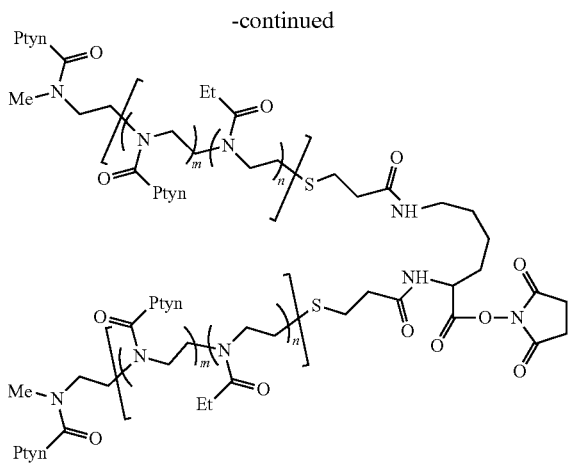

N-hydroxysuccinimide (0.0235 g, 0.204 mmol) and DCC (0.0421 g, 0.204 mmol) were added into a solution of {M-(PPtyn)$_2$(PEOZ)$_{18}$}$_2$-Lys-CO$_2$H (Mn 4200 Da, 0.832 g, 0.198 mmol) in dichloromethane (4 mL) at 0° C. After stirring for 2 hours in the cold, the mixture was warmed to room temperature and stirred overnight. The white precipitate was removed by filtration and the solution was added to diethyl ether to give a white powder. The powder was collected by filtration and dried under vacuum (0.8 g, 88% yield). The attachment of maleimide was shown by $^1$H NMR spectrum that shows the succinimidyl protons at 2.86 ppm (s, 2H) along with the usual backbone peaks. GPC showed 97% of the desired product (Mn=4550 Da, PD=1.04) and 3% of acid polymer.

To confirm product identity, the product (Mn 4550 Da, 0.103 g, 0.023 mmol) was treated with phenylethylamine (0.009 mL, 0.068 mmol) and triethylamine (0.009 mL, 0.068 mmol) in dichloromethane (3 mL). After stirring overnight, the mixture was filtered and added to diethyl ether. The white powder was isolated by filtration and dried under vacuum to provide the product in quantitative yield. According to GFC, the conversion yield was 99.7%.

Example 11

Synthesis of POZ-4[{-(PPtyn)$_2$(PEOZ)$_{18}$}$_2$-Lys]$_2$-Lys-ethyl ester

A solution of M-{(PPtyn)$_2$(PEOZ)$_{18}$}$_2$Lys-T-CO$_2$H (Mn=4200 Da, 0.415 g, 0.0988 mmol) and 1-HOBT (0.0318 g, 0.235 mmol) in acetonitrile (15 mL) was concentrated using rotary evaporation. The residue was dissolved in dry CH$_2$Cl$_2$ (3 mL) and then DCC (0.0291 g, 0.141 mmol) was added. After the mixture was stirred for 3 hours at room temperature, L-lysine ethyl ester dihydrochloride (0.0116 g, 0.047 mmol) and DMAP (0.0287 g, 0.235 mmol) were added. After stirring for 18 hours at room temperature, the mixture was filtered and added to ether (40 mL) to give a white precipitate. The precipitate was isolated by filtration and dried under vacuum to give the desired four-armed [{M-(PPtyn)$_2$(PEOZ)$_{18}$}$_2$-Lys]$_2$-Lys-ethyl ester as a white powder in quantitative yield. $^1$H NMR (Varian, 500 MHz, 10 mg/mL CDCl$_3$) showed the peak for Lys-Lys-Lys core molecule at 1.28 ppm (t, 3H, CH$_3$CH$_2$O—); 1.42 ppm (m, 6H, —C(=O)NHCH$_2$CH$_2$CH$_2$—); 1.54 ppm (m, 6H, —C(=O)NHCH$_2$CH$_2$—); 1.85 ppm (m, 6H, —CH$_2$CH(CO$_2$H)NH—); 4.14 ppm (br s, 2H, —CO$_2$CH$_2$CH$_3$) and 4.45 ppm (m, 3H, —CH$_2$CH(CO$_2$H)NH—) and peaks for pendant pentynyl group at 1.85 ppm (m, 2H, —CH$_2$CH$_2$O=CH); and 2.02 ppm (m, 1H, —CH$_2$CH$_2$C≡CH). GPC and GFC showed a mixture of main product (96%, Mn=7970 Da, PD=1.06) and excess of acid polymer (4%).

Example 12

Conjugation of Glucosamine and Zidovudine onto H-(Ptyn)$_4$(EOZ)$_{20}$-T-CO$_2$H After drying azeotropically with acetonitrile, H-(Ptyn)$_4$(EOZ)$_{20}$-T-CO$_2$H (0.18 g, 0.0619 mmol, Mn 2100 Da by MALDI) was dissolved in dichloromethane (2 mL). NHS (0.0071 g, 0.0619 mmol) and DCC (0.0128 g, 0.0619 mmol) were added at room temperature. After stirring overnight at room temperature, the mixture was filtered and precipitated by addition to diethyl ether. Diethyl ether solution was decanted and the residue was dried in vacuo to give the desired N-hydroxysuccinimide ester; i.e. H-(Ptyn)$_4$(EOZ)$_{20}$-T-SPA as a white powder in a quantitative yield. GFC shows purity and attachment of NHS was proved by $^1$H NMR showing the succinimidyl protons at 2.86 ppm (s, 4H).

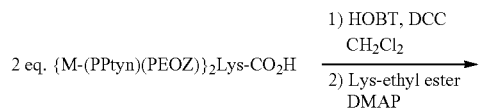

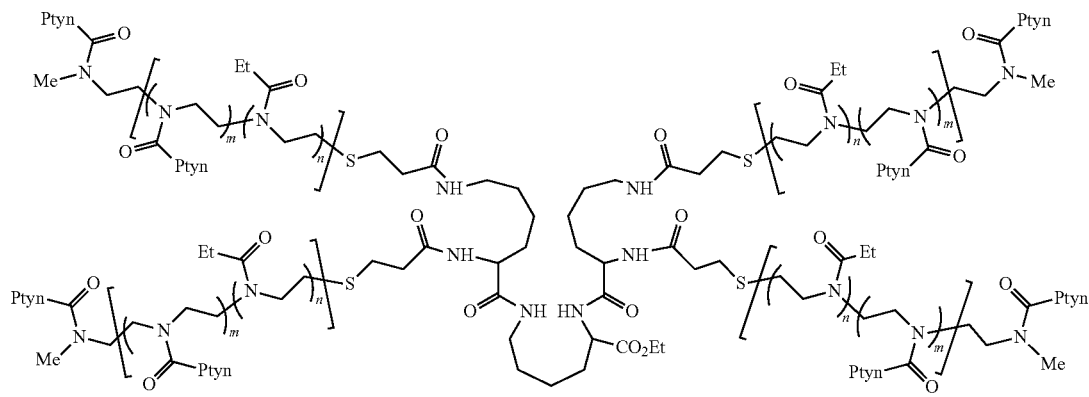

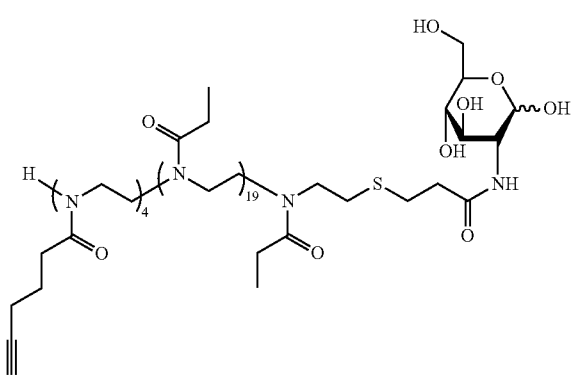

D(+)-glucosamine hydrochloride (0.137 g, 0.0663 mmol) was dissolved in 2 mL of 0.1 N boric acid solution followed by the adjustment of pH to 8.5 using 0.1 N NaOH solution. H-(Ptyn)$_4$(EOZ)$_{20}$-T-SPA (0.19 g, 0.0663 mmol, Mn 3000 Da) was added as a solid. The mixture was stirred for 3 hours at room temperature while maintaining pH at 8.5 using 0.1 N NaOH. The mixture was acidified (pH ~3) and extracted with dichloromethane. The combined organic phases were dried over anhydrous Na$_2$SO$_4$, filtered, concentrated, and dried in vacuo to give 0.14 g of pale yellow powder. The conjugation of glucosamine was confirmed by $^1$H NMR (Varian, 500 MHz, 10 mg/mL DMSO-d6) that shows the 2-position proton on glucoseamide at 4.92 ppm (s, 1H). Ion exchange chromatography showed a substitution yield of 83%.

H-(Ptyn)$_4$(EOZ)$_{20}$-T-Gluco (0.05 g, 0.0156 mmol, Mn 3200 Da) and the antiviral nucleoside zidovudine (AZT, 0.0167 g, 0.0625 mmol, 4 eq) were dissolved in water (2 mL). Sodium ascorbate (0.0012 g, 0.00625 mmol) and CuSO$_4$.5H$_2$O (0.0008 g, 0.00313 mmol) were added at room temperature. After stirring for 18 hours, water was removed using a rotary evaporator. The residue was dissolved in a 1:1 mixture of MeOH and CHCl$_3$ and then precipitated by addition to diethyl ether. Diethyl ether solution was decanted and the residue was dried in vacuo to give the desired product as a white powder in a quantitative yield. The 'click' coupling of the azide group on zidovudine to each acetylene pendant on the polymer chain was verified by NMR. $^1$H NMR (Varian, 500 MHz, 10 mg/mL DMSO-d6) shows that the polymer chain contained an average of units of thymidines with the thymidyl proton peaks at 11.3 ppm (br s, 1H, —OH), 8.05 ppm (s, 1H, triazole), 7.81 ppm (s, 1H), 6.41 ppm (t, 1H), 5.31 ppm (m, 1H), 5.26 ppm (m, 1H), 4.18 ppm (br s, 1H), and 1.80 (s, 3H). The 2-position proton on glucoseamide shows at 4.92 ppm (s, 1H). GPC gave Mn=4700 Da and Mp=4830 Da with PDI of 1.07.

Example 13

Conjugation of Irinotecan to POZ

Irinotecan.HCl.3H$_2$O (0.200 g, 0.295 mmol) was dissolved in acetonitrile (15 mL) and dried by azeotropic distillation. The residue was dissolved in dichloromethane (6 mL) and 6-azidohexanoic acid (0.0928 g, 0.591 mmol) was added. After the addition of dimethyaminopyridine (DMAP) (0.0722 g, 0.591 mmol) and dicyclohexylcarbodiimide (DCC) (0.122 g, 0.591 mmol), the resulting mixture was allowed to stir overnight at room temperature. The mixture was precipitated by addition to diethyl ether. The ether solution was decanted and the remaining precipitate was dried to give 0.144 g of the desired product as a pale yellow powder (67% yield). $^1$H NMR (Varian, 500 MHz, 10 mg/mL CDCl$_3$) δ 0.98 (t, 3H, C-9H), 1.41 (m, 2H, C-3H), 1.41 (m, 3H, C-18H), 1.41 (m, 2H, bipiperidyl H), 1.58 (m, 2H, C-4H), 1.58 (2H, bipiperidyl H), 1.70 (m, 2H, C-2H), 1.93 (m, 4H, bipiperidyl H), 2.16 (m, 1H, C-1H), 2.28 (m, 1H, C-1H), 2.32 (m, 1H, bipiperidyl H), 2.50 (m, 2H, C-5H), 2.50 (m, 2H, bipiperidyl H), 2.75 (m, 2H, C-17H), 2.94 (m, 1H, bipiperidyl C-3'H), 3.17 (m, 3H, bipiperidyl H), 3.25 (t, 2H, C-1H, —CH$_2$N$_3$), 3.55 (br s, 2H, bipiperidyl C-1'H and C-5'H), 4.56 (m, 2H, bipiperidyl C-1'H and C-5'H), 5.25 (s, 2H, C-14H), 5.41 (d, 1H, C-11H), 5.68 (d, 1H, C-11H), 7.19 (s, 1H, C-27H), 7.60 (d, 1H, C-22H), 7.87 (s, 1H, C-20H), 8.23 (d, 1H, C-23H).

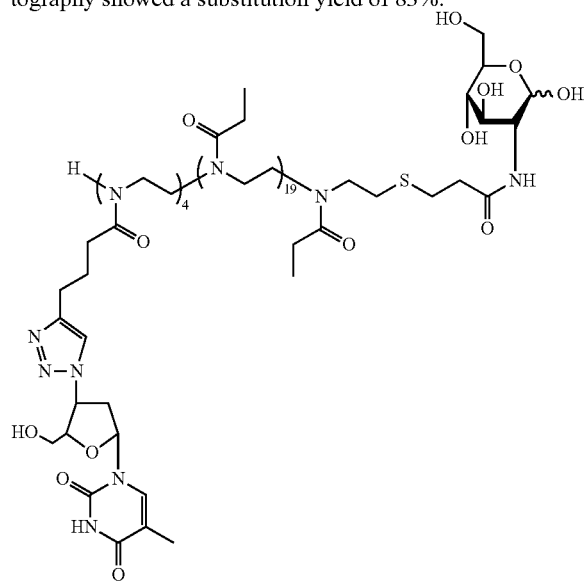

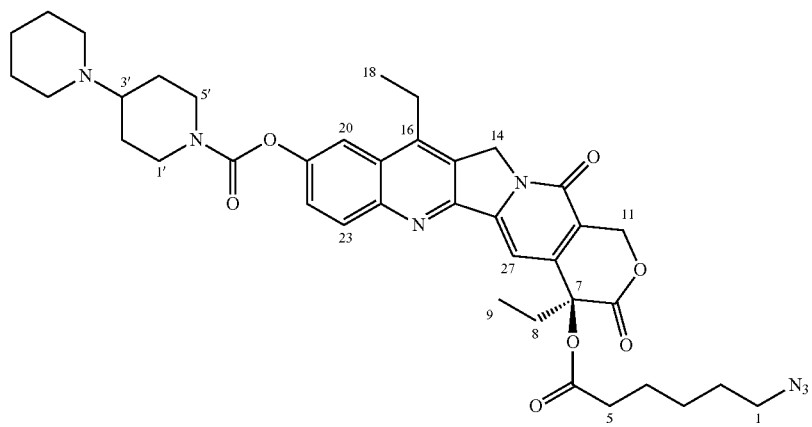 [SMILES: CCc1c2c(nc3ccc(OC(=O)N4CCC(N5CCCCC5)CC4)cc13)-c1cc3c(c(=O)n1C2)COC(=O)[C@@]3(CC)OC(=O)CCCCCN=[N+]=[N-]]

Conjugation of Random H-(Ptyn)$_4$(EOZ)$_{20}$-T-NH$_2$ and Irinotecan Azido Hexanoate

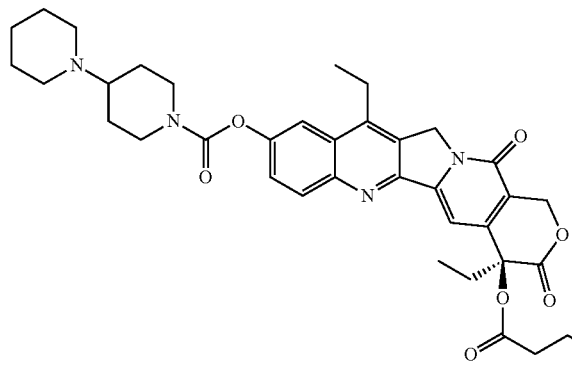
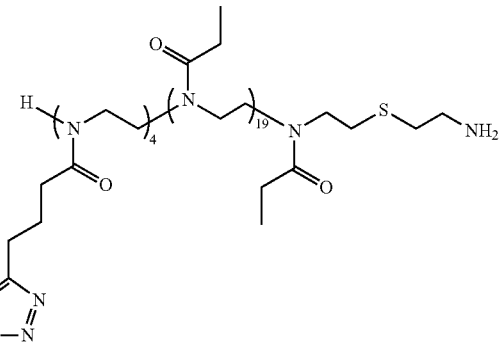

H-(Ptyn)$_4$(EOZ)$_{20}$-T-NH$_2$ (0.05 g, 0.0163 mmol, 1 eq., Mn 3070 Da), from a previous example, and irinotecan azido hexanoate (0.0473 g, 0.0652 mmol, 4 eq) were dissolved in water (2 mL) Sodium ascorbate (0.0013 g, 0.00652 mmol, 0.4 eq) and CuSO$_4$.5H$_2$O (0.0008 g, 0.00326 mmol, 0.2 eq) were added at room temperature. After stirring for 22 hours, water was removed using a rotary evaporator. The residue was dissolved in dichloromethane and then precipitated by addition to diethyl ether. Diethyl ether solution was decanted and the residue was dried in vacuo to give 0.7 g of the desired product as an off-white powder (72% yield). The 'click' coupling of the azide group (on irinotecan azido hexanoate) to the acetylene pendants (on POZ) was verified by NMR. $^1$H NMR (Varian, 500 MHz, 10 mg/mL CDCl$_3$) shows that the polymer chain contained an average of 4 units of irinotecans with the aromatic proton peaks of irinotecan at 7.14 ppm (t, 1H), 7.57 ppm (br s, 1H), and 7.85 ppm (br s, 1H), 8.16 ppm (br s, 1H), and new signals at 4.27 ppm (br s, 2H, adjacent to triazole —CH$_2$NR) and 7.40 ppm (br s, 1H, triazole). GPC gave Mn=4160 Da and Mp=4900 Da with PDI of 1.19.

What is claimed:

1. A heterofunctional polyoxazoline derivative of the general structure:

$R_1$—{[N(COX)CH$_2$CH$_2$]$_o$—[N(COR$_2$)CH$_2$—CH$_2$)]$_n$—[N(COY)CH$_2$—CH$_2$)]$_m$}$_a$—Z wherein:
R$_1$ is an initiating group;
R$_2$ is independently selected for each repeating unit from an unsubstituted or substituted alkyl, an unsubstituted or substituted alkenyl, an unsubstituted or substituted aralkyl or an unsubstituted or substituted heterocyclylalkyl group;
X is a pendent moiety containing a first functional group;
Y is a pendent moiety containing a second functional group;
Z is a terminating nucleophile, wherein Z is is S—U—W, wherein U is a linking group and W is a third functional group selected from the group consisting of: an alkyne, an amine, an oxyamine, an aldehyde, a ketone, an acetal, a ketal, an ester, a carboxylic acid, an activated carboxylic acid, an active carbonate, a chloroformate, an alcohol, an azide, a vinyl sulfone, a maleimide or orthopyridyl disulfide;
a is ran which indicates a random copolymer or block which indicates a block copolymer;
o and m are each an integer independently selected from 1-50;
n is an integer selected from 0-1000; and
wherein the first and second functional groups are chemically orthogonal to one another.

2. The heterofunctional polyoxazoline derivative of claim 1 wherein R$_1$ is a hydrogen, substituted or unsubstituted alkyl or substituted or unsubstituted aralkyl group.

3. The heterofunctional polyoxazoline derivative of claim 1 wherein the first and second functional groups are each independently an alkyne, an amine, an oxyamine, an aldehyde, a ketone, an acetal, a ketal, an ester, a carboxylic acid, an activated carboxylic acid, an active carbonate, a chloroformate, an alcohol, an azide, a vinyl sulfone, a maleimide or orthopyridyl disulfide.

4. The heterofunctional polyoxazoline derivative of claim 3 wherein the carboxylic acid is a negatively charged species and the amine is a positively charged species.

5. The heterofunctional polyoxazoline derivative of claim 1 wherein the first and second functional groups are each chemically orthogonal to the third functional group.

6. The heterofunctional polyoxazoline derivative of claim 1 wherein W is an alkyne, an amine, a carboxylic acid, or an activated carboxylic acid.

7. The heterofunctional polyoxazoline derivative of claim 1 wherein W is —CO$_2$H or —NH$_2$.

8. The heterofunctional polyoxazoline derivative of claim 1 wherein at least one of the first and second functional groups is chemically orthogonal to the third functional group.

9. The heterofunctional polyoxazoline derivative of claim 1 linked to at least one target molecule to form a target molecule-POZ conjugate.

10. The heterofunctional polyoxazoline derivative of claim 9, where the at least one target molecule is a therapeutic agent, a targeting agent or a therapeutic agent and a targeting agent.

* * * * *